United States Patent [19]

Melanon et al.

[11] Patent Number: 5,576,180
[45] Date of Patent: Nov. 19, 1996

[54] PRIMERS AND METHODS FOR SIMULTANEOUS AMPLIFICATION OF MULTIPLE MARKERS FOR DNA FINGERPRINTING

[75] Inventors: Serge B. Melançon, Outremont; Damian Labuda; Jian Q. Tang, both of Montréal; Michel Vanasse, Ville Mont-Royal, all of Canada

[73] Assignee: Centre de Recherche de l'Hôpital Ste-Justine, Quebec, Canada

[21] Appl. No.: 432,023

[22] Filed: May 1, 1995

[51] Int. Cl.$^6$ ................. C12Q 1/68; C12P 19/34; C07H 21/04
[52] U.S. Cl. ............... 435/6; 435/91.2; 536/24.3
[58] Field of Search ............ 435/6, 91.2; 536/24.3, 536/24.33

[56] References Cited

PUBLICATIONS

Sinnett, D. et al., 1988, Hum. Genet., 81:4–8.
Zietkiewicz, E. et al., 1992, Proc. Natl. Acad. Sci. USA., 89:8448–8451.
Tang et al., Mammalian Genome 6 :345–349 (1995).
The Stratagene Catalog (1988) p. 39.

*Primary Examiner*—Stephanie W. Zitomer
*Assistant Examiner*—Ethan Whisenant
*Attorney, Agent, or Firm*—Klauber & Jackson

[57] ABSTRACT

The present invention relates to a DNA amplification primer pair for the simultaneous amplification of multiple highly polymorphic genomic loci, which comprises R14B264/Q560mak (SEQ ID NO:1/SEQ ID NO:2). A method for the DNA fingerprinting identification of genetically related or unrelated individuals, which comprises the steps of: a) collecting genomic DNA sample of the individuals; b) performing DNA amplification of the DNA samples of step a) using the primer pair R14B264/Q560mak (SEQ ID NO:1/ SEQ ID NO:2); and c) separating the amplified DNA segments of step b); whereby three markers of the genomic DNA of different size are amplified and serve as DNA fingerprinting of the individuals.

6 Claims, 4 Drawing Sheets

FIG-1

PRIMERS AND METHODS FOR SIMULTANEOUS AMPLIFICATION OF MULTIPLE MARKERS FOR DNA FINGERPRINTING

BACKGROUND OF THE INVENTION (a) Field of the Invention

The invention relates to a PCR primer pair R14B264/Q560mak which correspond to the key sequences of the polymorphic loci and a method of DNA fingerprinting using these primers.

(b) Description of Prior Art

Creating a reliable genetic map is a necessary step towards understanding the structure and function of the human genome and discovering genes responsible for hereditary disorders. The map position eventually leads to characterization of a genetic defect and to elucidation of the underlying biochemistry. The wide-spread application of linkage mapping in humans was triggered by the introduction of RFLP-markers. Subsequently, more informative markers have been developed relying on allelic variation in tandemly repeated sequence motifs.

The use of polymerase chain reaction, PCR, opened new opportunities in DNA typing, increasing further the speed and resolution of this analysis.

Typically, genetic markers are typed one locus at a time. However, multiplexing has been also applied or proposed at different stages of the analysis. Simultaneous amplification of DNA from multiple genomic loci can be achieved by anchoring PCR primers in genomic interspersed repeats. Alu sequences were used in human while other dispersed short and/or simple sequence repeats found a much broader taxonomic application. Inter-Alu polymorphisms, revealed by PCR using a single Alu-specific primer, so called alumorphs, have been shown useful in mapping human genetic disorders. However, since these techniques are based on the use of a single locus marker they do not provide for a reliable identification tool in DNA fingerprinting of individuals. The statistical occurrence of one locus among several individuals is high. Accordingly, the single locus marker techniques can not be reliably used to identify genetically related individuals, which have a higher incidence of possessing the same locus then biologically non-related individuals.

However, to date there exists no primers which would allow for the simultaneous amplification of multiple highly polymorphic genomic loci.

It would be highly desirable to be provided with means for the simultaneous amplification of multiple highly polymorphic genomic loci, which would provide for a reliable DNA fingerprinting tool for the identification of individuals and even those of the same genetic family.

It would be highly desirable to be provided with a reliable method for DNA fingerprinting identification of genetically related or unrelated individuals.

SUMMARY OF THE INVENTION

One aim of the present invention is to provide means for the simultaneous amplification of multiple highly polymorphic genomic loci.

Another aim of the present invention is to provide for DNA amplification primer pair R14B264/Q560mak which correspond to the key sequences of the polymorphic loci.

Another aim of the present invention is to provide a method for the DNA fingerprinting identification of genetically related or unrelated individuals.

In accordance of the present invention, an Alu specific primer was used in a combination with another oligonucleotide. Although the first directs DNA synthesis from a variety of Alu elements, the second, which is radioactively labeled, narrows down the complexity of the electrophoretic pattern seen on the autoradiogram. Due to abundant polymorphisms in 3' Alu tails this approach allows for simultaneous amplification of highly polymorphic genomic loci.

In accordance with the present invention there is provided a DNA amplification primer pair for the simultaneous amplification of multiple highly polymorphic genomic loci, which comprises R14B264/Q560mak (SEQ ID NO:1/SEQ ID NO:2).

Also in accordance with the present invention there is provided a method for the DNA fingerprinting identification of genetically related or unrelated individuals, which comprises the steps of:

a) collecting genomic DNA sample of the individuals;

b) performing DNA amplification of the DNA samples of step a) using the primer pair R14B264/Q560mak (SEQ ID NO:1/SEQ ID NO:2); and c) separating the amplified DNA segments of step b);
whereby three markers of genomic DNA of different size are amplified and serve as DNA fingerprinting of the individuals.

Also in accordance with the present invention there is provided a kit comprising the primer pair of the present invention (R14B264/Q560mak) and the typed Q900, Q560 and Q120 DNAs and optionally including the necessary reagents for DNA amplification.

For the purpose of the present invention the following terms are defined below.

The term "primer" is intended to mean any oligonucleotide which can be used to direct DNA polymerization, more specifically the DNA amplification primer of the present invention consists in R14B264/Q560mak (SEQ ID NO:1/SEQ ID NO:2).

The term "marker" is intended to mean any polymorphic genomic locus, which may vary among individuals and serve as a DNA fingerprinting identification mean.

The term "three-marker PCR" is intended to mean any DNA amplification procedure simultaneously targeting three polymorphic genomic loci.

The term "asymmetric PCR" is intended to mean any DNA amplification reaction using unequal concentration of primers.

The term "Urea-PAG separation methods" is intended to mean any non-denaturing polyacrylamide gel electrophoresis using non-denaturing concentration of urea.

DETAILED DESCRIPTION OF THE INVENTION

The present invention relates to a PCR primer pair R14B264/Q560mak which are the key sequences of the polymorphic loci in this invention and are set forth as follows:

R14B264: 5' CAGAGCGAGACTCT 3'  (SEQ ID NO:1)

Q560mak: 5' GGTTACCCAGTGGTACCATT 3'  (SEQ ID NO:2)

The present invention also relates to a novel procedure to produce three-marker PCR using these primers using the asymmetric PCR and Urea-PAG separation methods.

Using the primers of the present invention, a specially designed asymmetric PCR amplifies three highly polymorphic markers, Q120, Q560 and Q900, which can be subsequently analyzed on an urea-PAG gel.

Some of the advantages of the primers and the method of the present invention are set forth below:

1. Three markers can be analyzed in a single experiment.
2. Very little specimen is required (~20 ng DNA or 10 μl of blood).
3. Very high combined Polymorphic Informative Content (cPIC=2.37).
4. Combined Allelic Frequencies (CAF):
   Rarest Alleles: A4(Q120)×A2(Q560)×A1(Q900)
   $0.0750 \times 0.0104 \times 0.014 = 1.092 \times 10^{-5}$
   Most Frequent Alleles: A3(Q120)×A5(Q560)× A11(Q900)
   $0.3750 \times 0.2917 \times 0.125 = 1.367 \times 10^{-2}$
5. Combined Genotype Frequency for diploid (CGF):
   All possible genotype frequencies are shown in
   Rarest Genotype (RG): (RA)×(RA)=$1.1925 \times 10^{-10}$
   Most Frequent Genotype (MFG): A1/A3(Q120)×A1/A5(Q560)×a6/a7(Q900)
   $0.1782 \times 0.1642 \times 0.0278 = 8.13 \times 10^{-4}$

TABLE 1

| All possible genotype frequencies (diploid) | | |
|---|---|---|
| Q120 | Q560 | Q900 |
| A1/A1 = 0.0564 | A1/A1 = 0.0791 | a1/a1 = 0.000193* |
| A1/A2 = 0.0890 | A1/A2 = 0.0058 | a1/a2 = 0.000720 |
| A1/A3 = 0.1782** | A1/A3 = 0.0762 | a1/a3 = 0.001546 |
| A1/A4 = 0.0356 | A1/A4 = 0.1466 | a1/a4 = 0.001150 |
| A1/A5 = 0.0594 | A1/A5 = 0.1642** | a1/a5 = 0.002320 |
| A2/A2 = 0.0352 | A1/A6 = 0.0118 | a1/a6 = 0.003480 |
| A2/A3 = 0.1406 | A2/A2 = 0.0001* | a1/a7 = 0.003080 |
| A2/A4 = 0.0282 | A2/A3 = 0.0028 | a1/a8 = 0.001930 |
| A2/A5 = 0.0468 | A2/A4 = 0.0054 | a2/a2 = 0.000773 |
| A3/A3 = 0.1406 | A2/A5 = 0.0060 | a2/a3 = 0.003100 |
| A3/A4 = 0.0562 | A2/A6 = 0.0004 | a2/a4 = 0.002300 |
| A3/A5 = 0.0938 | A3/A3 = 0.0183 | a2/a5 = 0.004640 |
| A4/A4 = 0.0056* | A3/A4 = 0.0706 | a2/a6 = 0.006960 |
| A4/A5 = 0.0188 | A3/A5 = 0.0790 | a2/a7 = 0.006180 |
| A5/A5 = 0.0156 | A3/A6 = 0.0056 | a2/a8 = 0.003860 |
| | A4/A4 = 0.0678 | a3/a3 = 0.003090 |
| | A4/A5 = 0.1520 | a3/a4 = 0.004600 |
| | A4/A6 = 0.0108 | a3/a5 = 0.009260 |
| | A5/A5 = 0.0851 | a3/a6 = 0.013900 |
| | A5/A6 = 0.0122 | a3/a7 = 0.012360 |
| | A6/A6 = 0.0004 | a3/a8 = 0.007720 |
| | | a4/a4 = 0.001710 |
| | | a4/a5 = 0.006900 |
| | | a4/a6 = 0.010360 |
| | | a4/a7 = 0.009200 |
| | | a4/a8 = 0.005740 |
| | | a5/a5 = 0.006940 |
| | | a5/a6 = 0.020800 |
| | | a5/a7 = 0.018500 |
| | | a5/a8 = 0.011560 |
| | | a6/a6 = 0.015600 |
| | | a6/a7 = 0.027800** |
| | | a6/a8 = 0.017360 |
| | | a7/a7 = 0.012300 |
| | | a7/a8 = 0.015420 |
| | | a8/a8 = 0.004820 | a1 = A1, A3, A9, A16, A22, A23
a2 = A2, A4, A5, A14, A17, A21
a3 = A6, A19
a4 = A7, A8, A18, A20
a5 = A10, A13
a6 = A11
a7 = A12
a8 = A15
*rarest genotype
**most frequent genotype The two rarest identical genotypes could be found only in a population of $8.39 \times 10^9$ individuals while the two most frequent identical genotypes could be found in population of $1.23 \times 10^3$ individuals.

Highly polymorphic locus Q900 has so far yielded 23 alleles in 72 chromosomes analyzed, but more alleles are expected as a larger population is analyzed.

Possible applications of the primers and the method of the present invention are listed without limitation:

As markers:
a) for gene mapping;
b) to assess paternity, maternity and identity of children;
c) in forensic science; and As a procedure to develop new multiloci markers.

As can be seen in Table 2, all three markers are very informative since most individuals analyzed are being heterologous in each of the three loci (polymorphic information contents from 0.71 and 0.95).

TABLE 2

Characteristics of the three-locus markers

| locus | chromosome analyzed | number of alleles | Frequencies of alleles | PIC | chromosomal localization | source of polymorphis |
|---|---|---|---|---|---|---|
| Q120 | 80 | 5 | A3 = 0,3750<br>A1 = 0,2375<br>A2 = 0,1875<br>A5 = 0,1250<br>A4 = 0,0750 | 0,71 | 5q31.2–33.3 | (AAT) 10–14 |
| Q560 | 96 | 6 | A5 = 0,2917<br>A1 = 0,2813<br>A4 = 0,2604<br>A3 = 0,1354<br>A6 = 0,0208<br>A2 = 0,0104 | 0,71 | 19q12 | (TAAA)7–12 |
| Q900 | 72 | 23 | A11 = 0.1250<br>A12 = 0.1111<br>A10,<br>A13 = 0.0833<br>A15 = 0.0694<br>A6,<br>A19 = 0.0556<br>A7,<br>A8,<br>A18,<br>A20 = 0.0414<br>A2,<br>A4,<br>A5,<br>A14,<br>A17,<br>A21 = 0.0278<br>A1,<br>A3,<br>A9,<br>A16,<br>A22,<br>A23,<br>A12 = 0.0139 | 0,95 | 17q12–q24 | $(AG)_n$<br>$(AAAGG)_m$ |

The markers of the present invention have been integrated into the CEPH families linkage map (Table 3). Whether the purpose is to map genes or to exclude mapping, three regions in different chromosomes may be screened in one experiment using the primers of the present invention.

TABLE 3

Assignment of alleles in CEPH individuals

| CEPH Samples | Q120 | Q560 | Q900 |
|---|---|---|---|
| 102/1 | A3, A5 | A4, A5 | A2, A4 |
| 102/2 | A1, A4 | A1, A5 | A11, A18 |
| 1331/12 | A1, A5 | A3, A4 | A8, A15 |
| 1331/13 | A2, A3 | A4, A5 | A3, A10 |
| 1331/14 | A3, A3 | A4, A5 | A12, A12 |
| 1331/15 | A2, A5 | A3, A5 | A12, A12 |
| 1347/12 | A2, A3 | A1, A3 | |
| 1347/13 | A1, ? | A1, A4 | |
| 1347/14 | A3, A3 | A5, A5 | |
| 1347/2 | A2, A3 | A1, A5 | |
| 1347/15 | A2, A3 | A1, A3 | |

Currently available DNA tests used to perform DNA fingerprinting in persons in or out of the Court Room, rely on poorly informative markers many of which are based on the technique of RFLP hybridization. Their informativity is poor and long periods of time are needed to perform the hybridization. Others have proposed two-dimensional DNA typing as an alternative. However, the latter procedure is more expensive and time consuming, and needs special equipment and laboratory personnel.

The combined advantages of the three-marker PCR technique of the present invention feature quickness (with even faster results when performed using an automatic DNA sequencer), very high informativity and no special requirements in terms of laboratory equipment and personnel. These advantages translate into low cost of operation.

The present invention will be more readily understood by referring to the following examples which are given to illustrate the invention rather than to limit its scope.

EXAMPLE I

Alu-PCR Combined with Non-Alu Primers to Reveal Multiple Polymorphic Loci

DNA samples

DNAs of CEPH (Centre d'Étude du Polymorphisme Humain) families 102, 884, 1331, 1332, 1347, 1362, 1413 and 1416 were provided by Dr. J. Weissenbach (Gen éthon, Paris) while those from unrelated volunteers were isolated from peripheral blood as described earlier (Sinnett, D. et al., 1988, *Hum. Genet.*, 81:4–8). BIOSMAP™ somatic cell hybrids DNAs Panel I and Panel II (lot #016) was purchased from BIOS Laboratories (new Haven, Conn. USA).

Polymerase Chain Reaction

In a reaction system that reveals the three-locus marker, 0.2 µM of the Alu primer R14B/246 5'CAG AGC GAG ACT CT3' and 1µM of the nested primer 5'GGT TAC CCA GTG GTA CCA TT3' (1 to 4 ratio 5'-[$^{32}$P]-labeled to cold) were used. Note that in order to increase the reaction specificity and suppress the unwanted inter-Alu amplification directed by R14B/264 alone, its concentration was lowered and the radioactive label was used at the nested primer only. The reaction mixture (20 µl) included 16 ng of genomic DNA, 1 unit of Taq™ DNA polymerase and 0.2 mM each of four dNTPs, in 10 mM Tris-HCl, pH 9.0, 50 mM KCl, 1.5 mM MgCl$_2$, 2% formamide, 0.01% gelatin and 0.01% Triton™ X-100. In a Perkin-Elmer Cetus™ thermal-cycler, 27 cycles were carried out: 94° C. for 30 sec, 55° C. for 45 sec and 72° C. for 45 sec; with a 7 min 72° C. incubation at the end. Reaction conditions for inter-Alu PCR and radioactive labeling were as described (Zietkiewicz, E. et al., 1992, *Proc. Natl. Acad. Sci. USA.*, 89:8448–8451).

Gel electrophoresis

For three-locus marker, the PCR products were loaded on a 0.4 mm thick (BioRad SequiGel™ 50×40 cm apparatus) native 6% polyacrylamide gel (acrylamide to N,N'methylene-bis-acrylamide ratio of 29:1) in 90 mM Tris-borate, pH 8.3, 2 mM EDTA and 3M of urea. The addition of 3M urea greatly improves the quality of the separation. The electrophoresis was carried out at room temperature at 14 volts/cm (i.e. 7000 V/gel) for a total of 6000 Vhrs and up to 20000 Vhrs in a population study of unrelated individuals for Q900.

Sequencing. DNA fragments identified by autoradiography were excised from a dried gel, extracted by incubation in 0.5M ammonium acetate, 0.1% SDS and 1 mM EDTA, ethanol precipitated and reamplified (Zietkiewicz, E. et al., 1993, *Proc. Natl. Acad. Sci. USA.*, 89:8448–8451). Sequencing was done on Applied Biosystems™ 373A DNA sequencer using fluorescent dye terminators and PCR primers described above.

Linkage analysis. Linkage analysis was performed using the LINKAGE™ package V5.2 for SunOS, and CEPH database V6.0. MLINK™ and CLODSCORE™ programs were used to calculate pairwise lodscores between the markers of the present invention and the CEPH™ markers. Recombination fractions between microsatellite markers, which were selected based on the results of two-point analysis with our markers, were computed by CLINK™ program using data from the 8 CEPH™ families. The positions of the codominant markers of the present invention on the resulting local maps were computed by CMAP™ program using segregation data from CEPH™ families. The closest CEPH™ markers of known cytogenetic location, as reported in Genome™ Data Base, GDB, were chosen and placed by CMAP™ on the local microsatellite maps as a reference.

Results and Discussion

A polymorphic band Q560 was cloned and sequenced, which was identified by inter-Alu PCR using the primer R14B/264 directing DNA amplification downstream from 3'termini of Alu elements. Its sequence contained an Alu repeat (underlined in FIG. 1), several (TAAA)-motifs and an 86 nucleotide segment with no similarity toward sequences reported in the GenBank database. Within this segment we designed a complementary oligonucleotide as a nested primer, for selective amplification of the corresponding Q560 locus.

Figure 1:
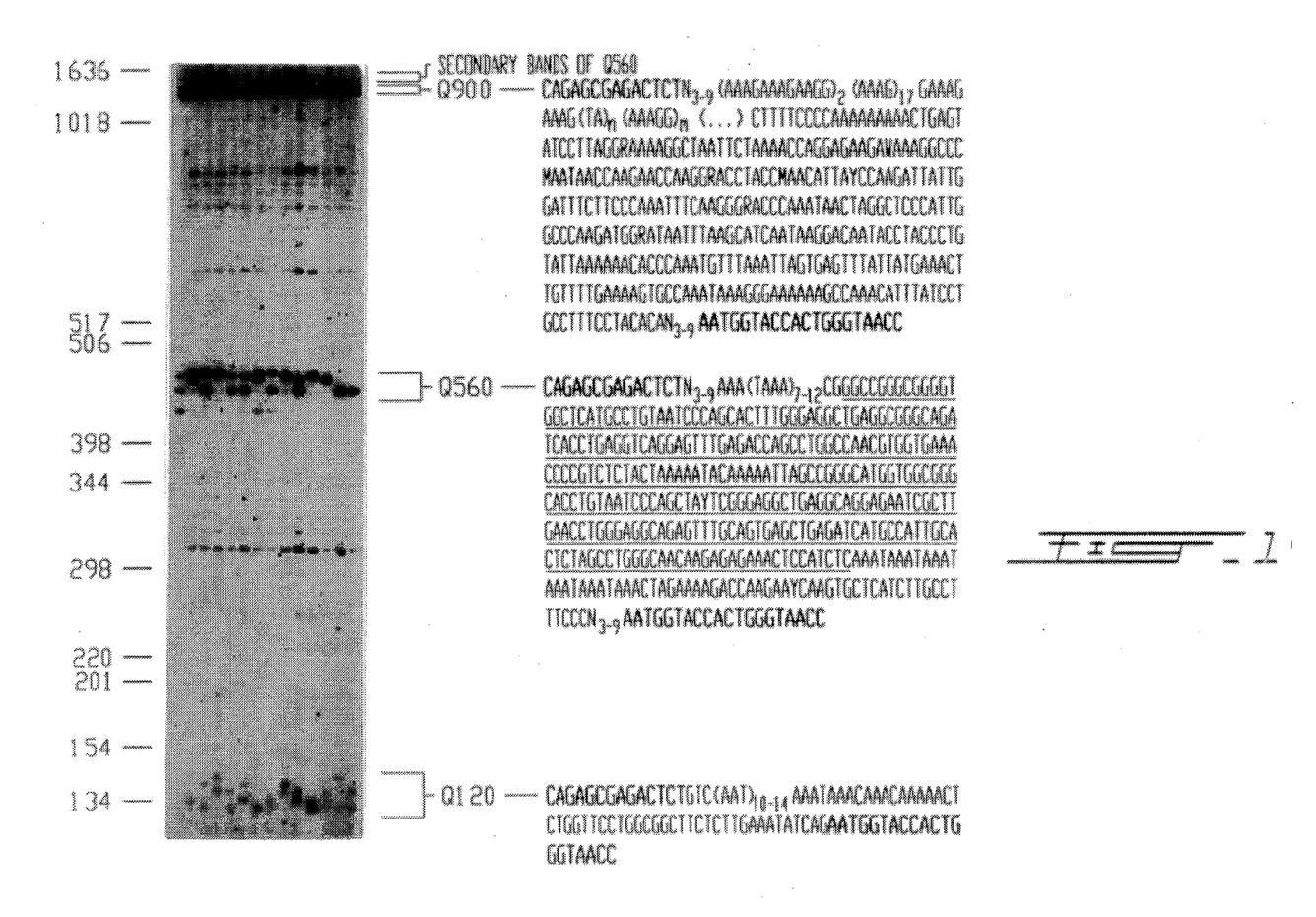
FIG. 1 shows the products of simultaneous amplification of three polymorphic loci analyzed by non-denaturing polyacrylamide gel electrophoresis (left), and their partial sequences revealing source of the length polymorphism (right)

As shown in FIG. 1, in addition to the expected allelic fragments from locus Q560 amplifications at two other polymorphic loci was also obtained, denoted Q120 and Q900. A series of bands migrating more slowly than the Q900 fragments represented the same pattern of polymorphisms as that seen among Q560 alleles in the middle of the gel (FIG. 1). Similar bands of 2–3 fold lower electrophoretic mobility were seen with Q900 but not with Q120 alleles. This phenomenon did not interfere with the analysis and was even useful by confirming the distribution of allelic bands (eg. Q560 polymorphisms in FIG. 1). It is likely that the slow migrating bands represent single strands resulting from an unbalanced amplification of the template strands.

In FIG. 1 no sequence similarity between these three PCR-products have been detected. Numbers on the left indicate migration of molecular weight marker (1 Kb DNA ladder, BRL). Primers are indicated in bold. The numbers n and m are not known exactly since the internal portion of Q900 sequence was not determined.

Figure 2A:
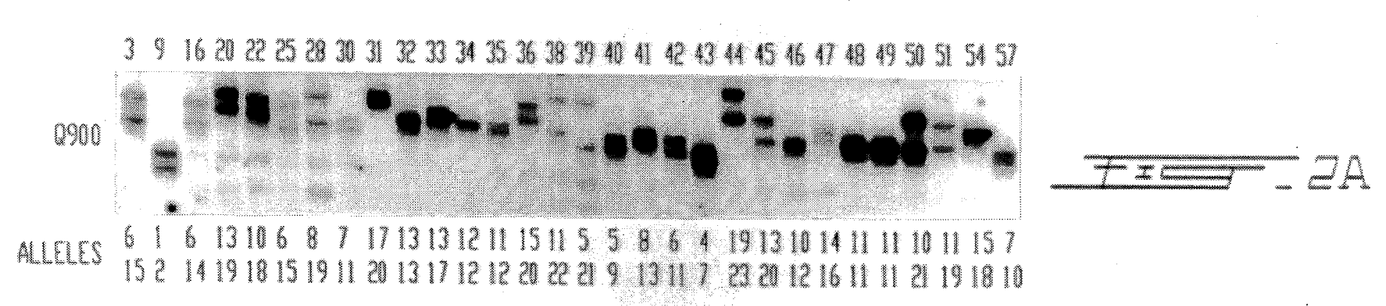
FIG. 2 shows the allelic forms of three loci in unrelated individuals (FIGS. 2A–2C) and their segregation in a CEPH family 102 (FIGS. 2D–2F)
Figure 2B:
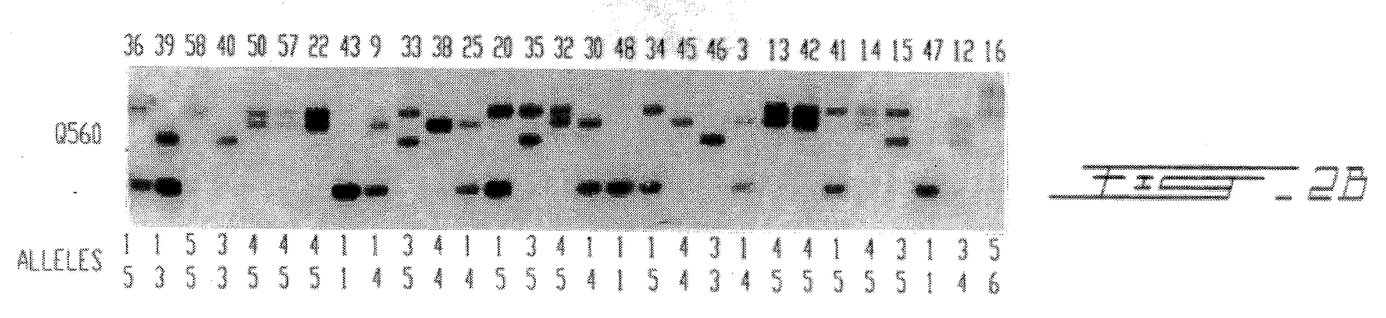
Figure 2C:
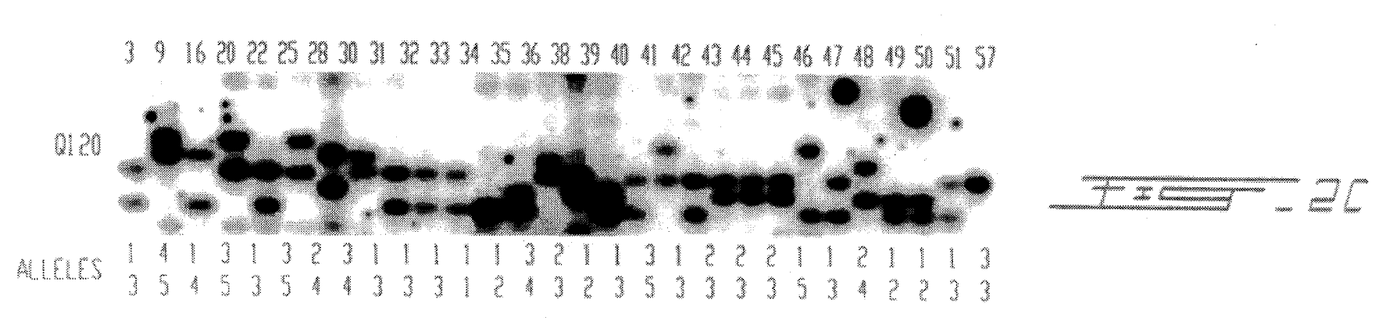
Figure 2D:
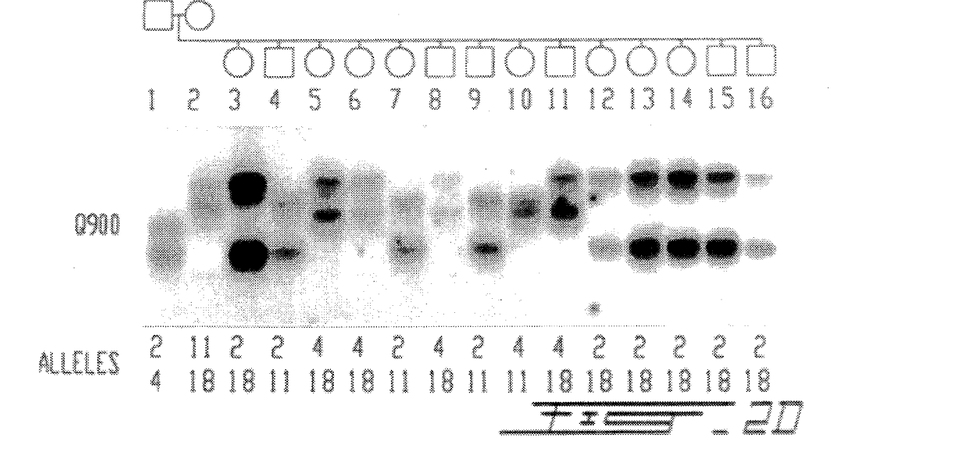
Figure 2E:
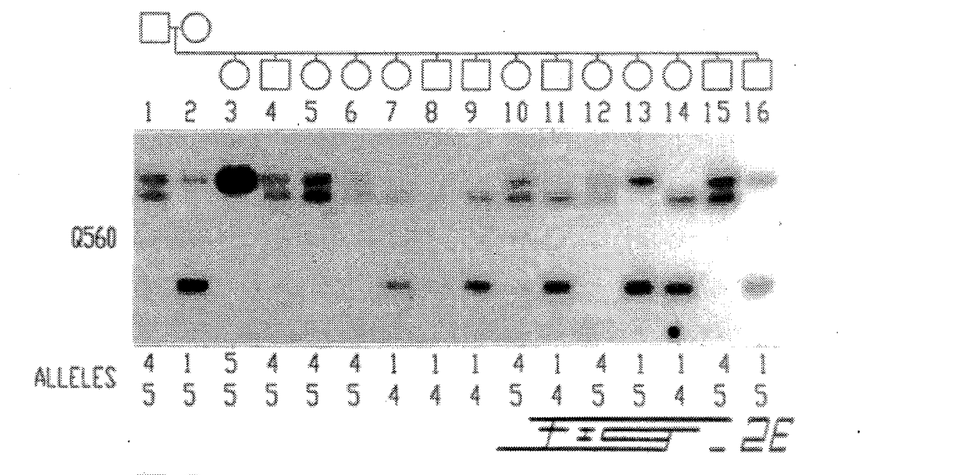
Figure 2F:
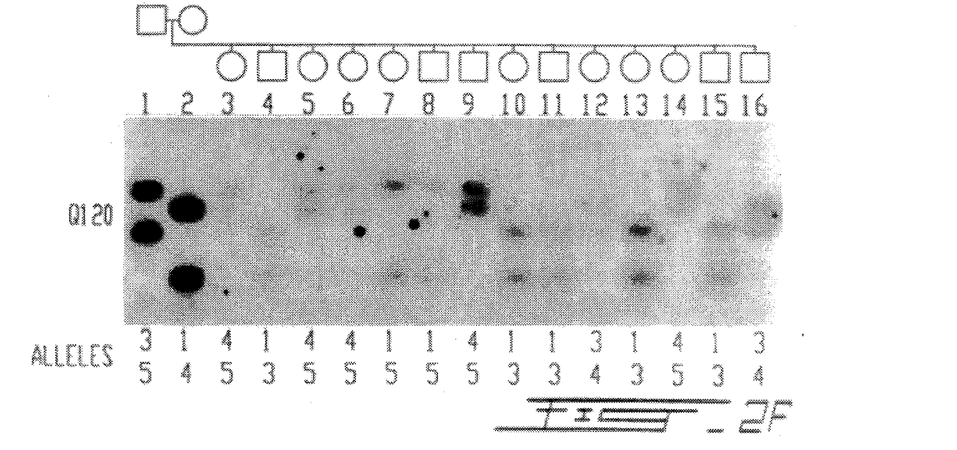

The number and distribution of alleles of the three-locus-marker have been studied in a sample of unrelated individuals (FIG. 2a). In FIGS. 2a and 2b, individual DNA samples are described on the top while numbers below identify the corresponding alleles.

The resulting data are summarized in Table 2 above. Several allelic bands of each locus were eluted from the gel and sequenced (FIG. 1). In Q120 and Q560 allelic differences were due to length polymorphism resulting from the variable number of (AAT) or (TAAA)-motifs, respectively. The greatest variability was observed in Q900 locus where 23 alleles were identified with frequencies ranging from 1/72 to 9/72. From the terminal sequences of five allelic variants of Q900 we identified the polymorphic region which contained a variable number of (AG) and (AAAGG)-repeats, and more complex (G+A) repeated motifs. Mendelian segregation within each locus of the marker was confirmed in three CEPH families and one such family is illustrated in FIG. 2b. The allele numbers assigned to CEPH grandparents and/or parents are listed in Table 3 above.

The chromosomal localization of the three loci was determined by PCR using DNA from a human-hamster somatic cell hybrid panel. This assignment was subsequently confirmed by a two-point linkage analysis with DNA markers from CEPH™ database V6.0 as well as by multipoint analysis to place then on a microsatellite map. Finally, their position was correlated with the closest CEPH™ markers of known cytogenetic location as shown in FIG. 3 (see also Table 2 above).

Figure 3A:
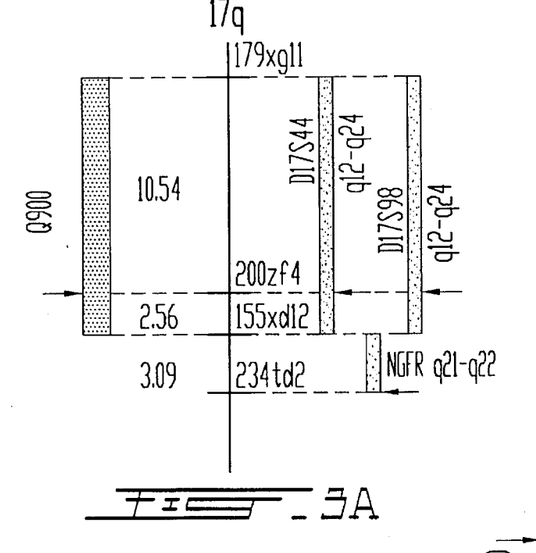
FIG. 3 (FIGS. 3A–3C) illustrates the localization of loci Q120, Q560 and Q900 on the local microsatellite maps of chromosomes 5, 19 and 17, respectively.
Figure 3B:
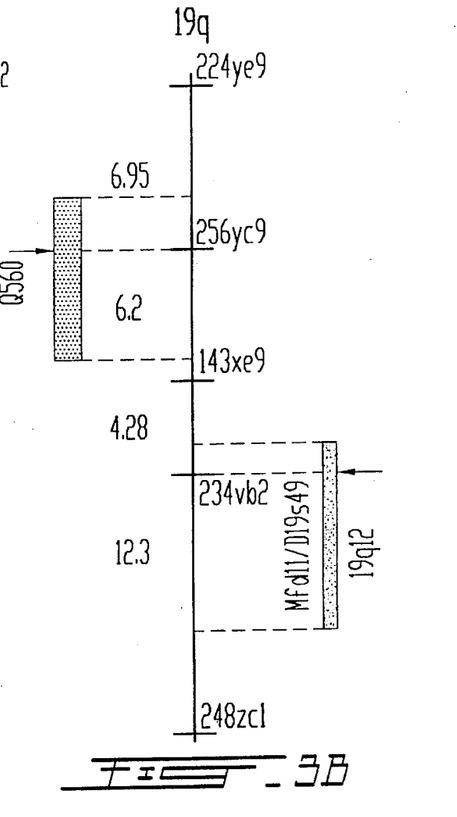
Figure 3C:
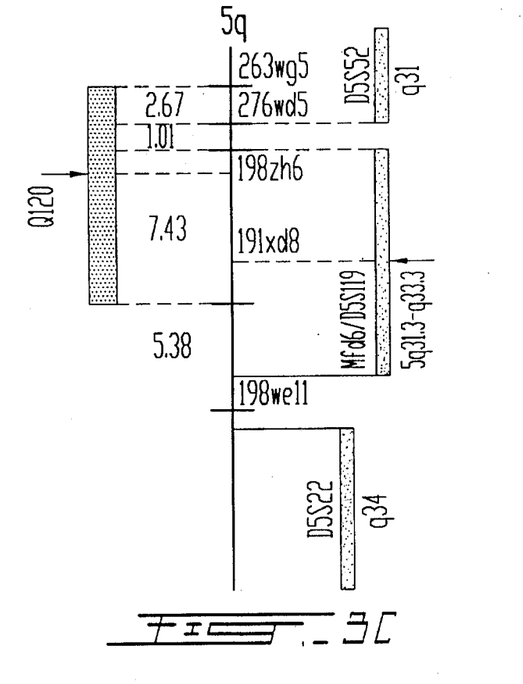

In FIG. 3, the maps show the best-supported order of microsatellite markers and genetic distance (sex average) between adjacent loci calculated by Kosambi map function. For chromosomes 19 and 17 the order of the microsatellite markers is resolved with odds greater than 1000:1. Ordering of the loci 276wd5 and 198zh6 (chromosome 5) with respect to each other has been only 1.35:1 odds; however, the inversion of these loci does not change position of the marker Q120. The names of microsatellite markers are shown on the right of each map and genetic distances on the left. Relative positions of our markers are indicated by bars on the left of each map; arrows point to the best position based on the location score analysis with respect to the microsatellite map. Positions of the reference CEPH-markers with known physical assignments are shown by bars on the right.

The different chromosomal location of each of these loci is consistent with random distribution of Alu-related polymorphisms.

The usefulness of DNA markers for genetic mapping can be described by their per locus informativity expressed by PIC and by the "multiplex ratio", estimating the number of polymorphic loci that can be scored during a single experiment. High per locus informativity characterizes codominant markers with multiple allelic length variants such as microsatellites. Concomitant amplification of several polymorphic sites can be achieved by using primers of random sequence or those complementary to interspersed repeats but the resulting markers either are, or are being coded as dominant ones, with maximum per locus PIC of 0.25. Here, taking advantage of frequent length variation in Alu-tails, a marker was obtained by combining high PIC and an increased multiplex ratio. The resulting combined PIC value is 2.37, obtained by summing up PIC values of contributing polymorphisms which are simultaneously analyzed (see Table 2 above).

enhances this effect which, together with the fact that Alu-tails are especially abundant in length polymorphisms, appears to be essential for our approach to work.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

---

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear     ( i i ) MOLECULE TYPE: DNA     ( i i i ) HYPOTHETICAL: NO     ( i v ) ANTI-SENSE: YES     ( x i ) SEQUENCE DESCRIPTION: SEQ ID NO:1:

CAGAGCGAGA CTCT                                14

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: DNA     ( i i i ) HYPOTHETICAL: NO     ( i v ) ANTI-SENSE: YES     ( x i ) SEQUENCE DESCRIPTION: SEQ ID NO:2:

GGTTACCCAG TGGTACCATT                        20

---

To account for multi-locus priming, an explanation proposed is that the "downstream-Alu-primer" represents a low-copy repeat. Our experience indicates that different pairs consisting of a labeled locus-specific primer, and a cold Alu-specific primer always lead to the amplification of a variety of DNA bands, in addition to the expected fragment. It appears that oligonucleotides of a moderate length often prime at other than the specified locus. However, only the presence of another primer, complementary to abundant and ubiquitous repeats, allows combination of the priming sites within amplifiable distance and thus leads to a variety of PCR-products. The complexity of DNA downstream of Alu repeats being often lower than the genomic average

We claim:

1. A DNA amplification primer pair for the simultaneous amplification of multiple highly polymorphic genomic loci, which consists of R14B264/Q560mak (SEQ ID NO:1/SEQ ID NO:2).

2. A method for the DNA fingerprinting identification of genetically related or unrelated individuals, which comprises the steps of:

a) collecting genomic DNA sample of said individuals;

b) performing DNA amplification of said DNA samples of step a) using the primer pair R14B264/Q560mak (SEQ ID NO:1/SEQ ID NO:2); and c) separating said amplified DNA segments of step b); whereby three markers of said genomic DNA of different size are amplified and serve as DNA fingerprinting of said individuals.

3. The method of claim 2, wherein said DNA amplification of step b) is effected by PCR or by asymmetric PCR procedure.

4. The method of claim 2, wherein said DNA separation of step c) is effected using a DNA sequencer or a gel electrophoresis procedure.

5. The method of claim 4, wherein said gel electrophoresis procedure is a urea-PAG separation method.

6. A kit for simultaneous amplification of multiple highly polymorphic genomic loci, which comprises:

a) R14B264/Q560mak (SEQ ID NO:1/SEQ ID NO:2); and b) typed Q900, Q560 and Q120 DNAs.

* * * * *

UNITED STATES PATENT AND TRADEMARK OFFICE
CERTIFICATE OF CORRECTION

PATENT NO.   : 5,576,180
DATED        : Nov. 19, 1996
INVENTOR(S)  : Serge B. Melanon, et al It is certified that error appears in the above-identified patent and that said Letters Patent is hereby corrected as shown below:

On title page, item [19] "Melanon et al." Should read --Melancon et al.--
Item [75] "Melan con" should read --Melancon--

Signed and Sealed this

Sixth Day of October, 1998

Attest:

BRUCE LEHMAN

*Attesting Officer*          *Commissioner of Patents and Trademarks*

UNITED STATES PATENT AND TRADEMARK OFFICE
CERTIFICATE OF CORRECTION

PATENT NO. : 5,576,180
DATED : Nov. 19, 1996
INVENTOR(S) : Serge B. Melanon, et al It is certified that error appears in the above-identified patent and that said Letters Patent is hereby corrected as shown below:

On drawing sheet, Fig. 1, in loci Q900, the second line of the loci, change "$(TA)_n$" to --$(AG)_n$--

Signed and Sealed this

Sixteenth Day of March, 1999

Q. TODD DICKINSON

Attest:

Attesting Officer

Acting Commissioner of Patents and Trademarks